(12) United States Patent
Schmid et al.

(10) Patent No.: US 11,497,741 B2
(45) Date of Patent: Nov. 15, 2022

(54) GRANULES CONTAINING DIAMINE DERIVATIVE

(71) Applicant: DAIICHI SANKYO COMPANY, LIMITED, Tokyo (JP)

(72) Inventors: Wolfgang Schmid, Pfaffenhofen (DE); Maren Kuhli, Pffaffenhofen (DE); Christoph Schuh, Pfaffenhofen (DE)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 142 days.

(21) Appl. No.: 17/255,721

(22) PCT Filed: Jun. 26, 2019

(86) PCT No.: PCT/JP2019/025363
§ 371 (c)(1),
(2) Date: Dec. 23, 2020

(87) PCT Pub. No.: WO2020/004456
PCT Pub. Date: Jan. 2, 2020

(65) Prior Publication Data
US 2021/0267954 A1    Sep. 2, 2021

(30) Foreign Application Priority Data

Jun. 27, 2018  (JP) .............................. JP2018-121423

(51) Int. Cl.
*A61K 31/444* (2006.01)
*A61K 9/08* (2006.01)
*A61K 9/16* (2006.01)

(52) U.S. Cl.
CPC .............. *A61K 31/444* (2013.01); *A61K 9/08* (2013.01); *A61K 9/1623* (2013.01); *A61K 9/1635* (2013.01); *A61K 9/1652* (2013.01); *A61K 9/1694* (2013.01)

(58) Field of Classification Search
CPC .. A61K 31/444; A61K 9/1623; A61K 9/1694; A61K 47/26
See application file for complete search history.

(56) References Cited

U.S. PATENT DOCUMENTS

| 9,402,907 | B2 | 8/2016 | Ishidoh et al. |
| 2008/0161417 | A1 | 7/2008 | Zhao |
| 2009/0137645 | A1 | 5/2009 | Zhang et al. |
| 2009/0324794 | A1 | 12/2009 | Duflot et al. |
| 2013/0022683 | A1 | 1/2013 | Kamada et al. |
| 2015/0110880 | A1 | 4/2015 | Sekiguchi et al. |
| 2015/0342938 | A1 | 12/2015 | Kojima et al. |
| 2017/0231969 | A1 | 8/2017 | Raneburger et al. |

FOREIGN PATENT DOCUMENTS

| JP | 2009544674 A | 12/2009 |
| JP | 2012036140 A | 2/2012 |
| JP | 2017008112 A | 1/2017 |
| JP | 2017523149 A | 8/2017 |
| WO | 2006119697 A1 | 11/2006 |
| WO | 2011115067 A1 | 9/2011 |

OTHER PUBLICATIONS

International Search Report corresponding to PCT/JP2019/025363 dated Sep. 24, 2019.
Written Opinion of the International Searching Authority corresponding to PCT/JP2019/025363 dated Sep. 13, 2019 in Japanese language.
Extended European Search Report dated Feb. 18, 2022 for corresponding European Patent Application No. 19825281.9-1109 and Patent No. 3815686 PCT/JP2019025363, 10 pages.

*Primary Examiner* — Robert A Wax
*Assistant Examiner* — William Craigo
(74) *Attorney, Agent, or Firm* — Locke Lord LLP; Nicholas J. DiCeglie, Jr.

(57) ABSTRACT

Provision of a granular preparation that contains edoxaban or a pharmacologically acceptable salt thereof, and has the property of being rapidly dissolved or suspended by the addition of water. A granular preparation comprising first granules containing (A) edoxaban or a pharmacologically acceptable salt thereof, (B) a sugar alcohol, and (C) a water-swelling additive, and second granules containing (D) 0.5 to 10% by weight of carmellose sodium with respect to the total weight of the preparation, and (E) 70 to 90% by weight of xylitol or sorbitol with respect to the total weight of the preparation.

30 Claims, 2 Drawing Sheets

| A: center, top |
| B: center, middle |
| C: center, bottom |
| D: front, middle, left |
| E: front, middle |
| F: right, top |
| G: back, top |
| H: back, left, middle |
| I: right, back, top |
| J: front, right, close to container wall |

GRANULES CONTAINING DIAMINE DERIVATIVE

CROSS REFERENCE TO RELATED APPLICATIONS

This Application is the National Phase entry under 35 U.S.C. § 371 of PCT International Application No. PCT/JP2019/025363, filed Jun. 26, 2019, which application claims priority to Japanese Patent Application No. 2018-121423 filed on Jun. 27, 2018. The entire contents of these applications are incorporated herein by reference in their entirety.

TECHNICAL FIELD

The present invention relates to a granular preparation containing edoxaban or a pharmacologically acceptable salt thereof and having the property of being rapidly dissolved or suspended by the addition of water.

BACKGROUND ART $N^1$-(5-Chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

[Formula 1]

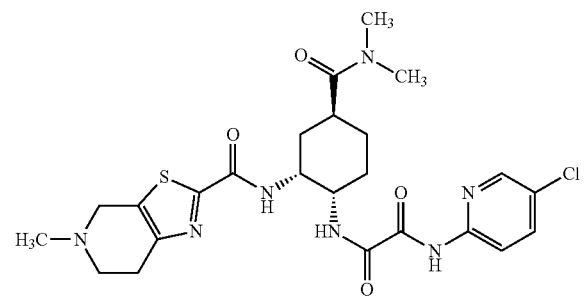

(I)

has the generic name edoxaban. Edoxaban exerts an antithrombotic effect by selectively, reversibly and directly inhibiting activated blood coagulation factor X (FXa), which has the effect of forming a thrombus by converting prothrombin to thrombin and promoting fibrin formation in the blood coagulation cascade (Patent Literature 1).

A large number of dosage forms such as tablets, capsules, granular preparations and powders are known as dosage forms for oral solid preparations in the fields of pharmaceutical and food products. Among such dosage forms, dosage forms such as granular preparations, dry syrups, oral jellies and orally disintegrating tablets have received attention in recent years as dosage forms that are easier to take for patients with dysphagia such as elderly people or children, and are under active development.

Oral jellies contain a large amount of water and have moderate fluidity. Therefore, oral jellies are easy to take for patients with low or reduced ability to swallow. Also, oral jellies are excellent in terms of portability, and their doses are adjustable. Furthermore, oral jellies are a dosage form suitable even for children because of having sweetness and suppressing the bitterness of drugs. However, oral jellies, which contain a large amount of water, require the dissolving or dispersing of drugs in water in the production process. As a result, a problem thereof is the difficulty in maintaining the stability of the drugs over a long period.

Orally disintegrating tablets possess both the property of rapidly disintegrating in the oral cavity and the property of sufficient hardness that can resist physical impact upon production, transport or use, as with usual tablets. For these reasons, orally disintegrating tablets have widespread support as a dosage form preferred for patients with reduced ability to swallow. However, most launched orally disintegrating tablets are commercialized with a specification intended for adults, and the general properties of the tablets are not suitable for fine dose adjustment. Therefore, orally disintegrating tablets still have problems associated with suitability as a dosage form for children.

Granular preparations, which are preparations in a powdery or granular form, are excellent in portability and are easy to take, even for patients with low or reduced ability to swallow such as elderly people or children. In addition, fine dose adjustment can also be performed according to the body weights of recipient patients. For these reasons, granular preparations contribute to improvement in drug compliance and have widespread support as a dosage form preferred for patients with reduced ability to swallow, particularly, children. Furthermore, granular preparations are preferred because the granular preparations can include sweetness in order to reduce the bitterness of active ingredients.

Granules for oral an suspension and dry syrups are preparations in a granular form that become suspensions or aqueous solutions when water is added thereto, and are typically dissolved or suspended in use. In addition to the portability of granular preparations, granules for an oral suspension and dry syrups are excellent because they are rapidly dissolved or suspended by the addition of water and can be orally administered as a solution or a suspension. Granules for an oral suspension and dry syrups can be administered, after dissolved or suspended, using an oral syringe on a volume basis.

Granular preparations for patients with reduced ability to swallow have previously been reported as follows: Patent Literature 2 describes an invention relating to a granular preparation comprising the hydrophobic drug loratadine, and a cellulose analog and/or a natural polymer. The invention is characterized by eliminating the need for a surfactant or a defoaming agent conventionally required for producing granular preparations of hydrophobic drugs. However, this document makes no mention of a granular preparation containing edoxaban or a pharmacologically acceptable salt thereof and having the properties of being rapidly dissolved or suspended by the addition of water as described in the present invention.

Patent Literature 3 describes an invention relating to a granular preparation containing a poorly water-soluble drug and 0.5 (w/w) % or more of hydroxypropylcellulose whose 2 (w/v) % aqueous solution has a viscosity of lower than 3.0 mPa·s at 20° C. However, this document makes no mention of a granular preparation containing edoxaban or a pharmacologically acceptable salt thereof as an active ingredient.

Meanwhile, examples of inventions relating to pharmaceutical compositions comprising edoxaban or a pharmacologically acceptable salt thereof include the following: Patent Literature 4 describes an invention relating to a pharmaceutical composition containing (a) edoxaban or a pharmacologically acceptable salt thereof, or a hydrate of the compound or the salt, (b) one or two or more components selected from a sugar alcohol and a water-swelling additive.

Patent Literature 5 describes an invention relating to a pharmaceutical composition with an adjusted content of edoxaban or a pharmacologically acceptable salt thereof.

Patent Literature 6 describes an invention relating to granules containing edoxaban or a pharmacologically acceptable salt thereof and granulated by keeping the maximum water content of granules during the granulation at 10% or less.

Patent Literature 7 describes an invention relating to a pharmaceutical composition containing edoxaban or a pharmacologically acceptable salt thereof, and an organic acid.

However, Patent Literature 4 to 7 make no mention of an invention relating to granular preparations containing edoxaban or a pharmacologically acceptable salt thereof and having the property of being rapidly dissolved or suspended by the addition of water.

CITATION LIST

Patent Literature

Patent Literature 1: U.S. Pat. No. 7,365,205
Patent Literature 2: U.S. Patent Application Publication No. 2008064713
Patent Literature 3: International Publication No. WO 2005/009474
Patent Literature 4: U.S. Pat. No. 9,149,532
Patent Literature 5: U.S. Pat. No. 8,449,896
Patent Literature 6: U.S. Patent Application Publication No. 20130022683
Patent Literature 7: U.S. Pat. No. 9,402,907

SUMMARY OF INVENTION

Technical Problem

Edoxaban is known to exhibit good solubility in a strongly acidic aqueous solution but to have reduced solubility (water solubility) in a neutral aqueous solution (a neutral buffer solution) (Patent Literature 4). Under the circumstances, the present inventors have conducted diligent studies to provide a granular preparation with high dissolution properties and easily taken even by patients with reduced ability to swallow such as elderly people or children, and consequently found that a granular preparation containing edoxaban and a high content of xylitol or sorbitol in the same granule has a reduced content of edoxaban in the produced preparation due to high hygroscopicity of xylitol and sorbitol, and is therefore poor in terms of manufacturability. Further, the present inventors found that edoxaban develops bitterness in the oral cavity.

An object of the present invention is to provide a granular preparation that contains edoxaban or a pharmacologically acceptable salt thereof, is rapidly dissolved or suspended by the addition of water, has excellent dissolution properties, and reduces the bitterness of the active ingredient.

Another object of the present invention is to provide a granular preparation containing edoxaban or a pharmacologically acceptable salt thereof and a high content of xylitol or sorbitol, having good manufacturability and having no reduction in the content of the active ingredient, and a method for producing the same.

Another object of the present invention is to provide a granular preparation excellent in terms of the uniformity of dosage units, without the separation of mixed particles caused by differences in particle size between particles when two types of granules, i.e., drug-containing granules containing edoxaban or a pharmacologically acceptable salt thereof and drug-free granules containing neither of them, are mixed (hereinafter, this phenomenon is also referred to as segregation), and a method for producing the same.

Solution to Problem

The present inventors have conducted diligent studies to attain the objects and consequently completed the present invention by finding that the objects are attained by a granular preparation comprising first granules containing (A) edoxaban or a pharmacologically acceptable salt thereof, (B) a sugar alcohol, and (C) a water-swelling additive, and second granules containing (D) 0.5 to 10% by weight of carmellose sodium with respect to the total weight of the preparation, and (E) 70 to 90% by weight of xylitol or sorbitol with respect to the total weight of the preparation.

Specifically, the present invention relates to the following [1] to [32]:

[1]

A granular preparation comprising
first granules containing
(A) edoxaban or a pharmacologically acceptable salt thereof,
(B) a sugar alcohol, and
(C) a water-swelling additive, and
second granules containing
(D) 0.5 to 10% by weight of carmellose sodium with respect to the total weight of the preparation, and
(E) 70 to 90% by weight of xylitol or sorbitol with respect to the total weight of the preparation.

[2]

The granular preparation according to [1], wherein the ratio ($R_2/R_1$) of the median size of the second granules ($R_2$) to the median size of the first granules ($R_1$) is 0.75 to 1.75.

[3]

The granular preparation according to [1], wherein the median size (X50) of the first granules is 130 μm to 240 μm, and the median size (X50) of the second granules is 170 μm to 240 μm.

[4]

The granular preparation according to any one of [1] to [3], wherein the granular preparation comprises 0.3 to 10% by weight of edoxaban or a pharmacologically acceptable salt thereof (A) with respect to the total weight of the preparation.

[5]

The granular preparation according to any one of [1] to [4], wherein edoxaban or a pharmacologically acceptable salt thereof (A) is edoxaban tosylate monohydrate.

[6]

The granular preparation according to any one of [1] to [5], wherein the sugar alcohol (B) is D-mannitol, xylitol, or erythritol.

[7]

The granular preparation according to [6], wherein the sugar alcohol (B) is D-mannitol.

[8]

The granular preparation according to any one of [1] to [7], wherein the granular preparation comprises 3 to 15% by weight of the sugar alcohol (B) with respect to the total weight of the preparation.

[9]
The granular preparation according to any one of [1] to [8], wherein the water-swelling additive (C) is pregelatinized starch and/or crystalline cellulose.
[10]
The granular preparation according to [9], wherein the water-swelling additive (C) is pregelatinized starch.
[11]
The granular preparation according to any one of [1] to [10], wherein the granular preparation comprises 1 to 10% by weight of the water-swelling additive (C) with respect to the total weight of the preparation.
[12]
The granular preparation according to any one of [1] to [11], further comprising a disintegrant.
[13]
The granular preparation according to [12], wherein the disintegrant is contained in the first granules.
[14]
The granular preparation according to [12] or [13], wherein the disintegrant is crospovidone and/or sodium carboxymethyl starch.
[15]
The granular preparation according to [14], wherein the disintegrant is crospovidone.
[16]
The granular preparation according to any one of [1] to [15], further comprising a binder.
[17]
The granular preparation according to [16], wherein the binder is contained in the first granules.
[18]
The granular preparation according to [16] or [17], wherein the binder is hydroxypropylcellulose.
[19]
The granular preparation according to any one of [1] to [18], wherein the granular preparation is granules for an oral suspension or a dry syrup.
[20]
The granular preparation according to [19], wherein the granular preparation is granules for an oral suspension.
[21]
The granular preparation according to [19], wherein the granular preparation is a dry syrup.
[22]
The granular preparation according to any one of [1] to [21], wherein the granular preparation is used as an aqueous solution or an aqueous suspension.
[23]
An aqueous solution or an aqueous suspension of the granular preparation according to any one of [1] to [21].
[24]
Use of the granular preparation according to any one of claims 1 to 21 as an aqueous solution or an aqueous suspension.
[25]
A method for producing a granular preparation, comprising
a step of obtaining first granules obtained by wet-granulating
(A) edoxaban or a pharmacologically acceptable salt thereof,
(B) D-mannitol,
(C) pregelatinized starch,
(D) crospovidone, and
(E) hydroxypropylcellulose
using water or an aqueous solution of the hydroxypropylcellulose (E),
a step of obtaining second granules obtained by wet-granulating
(F) 0.5 to 10% by weight of carmellose sodium with respect to the total weight of the preparation, and
(G) 70 to 90% by weight of xylitol or sorbitol with respect to the total weight of the preparation using water or an aqueous solution of the carmellose sodium (F), and
a step of mixing the first granules and the second granules obtained.
[26]
The production method according to [25], wherein the wet granulation is fluidized-bed granulation.
[27]
The method according to [25] or [26], wherein the ratio ($R_2/R_1$) of the median size of the second granules ($R_2$) to the median size of the first granules ($R_1$) is 0.75 to 1.75.
[28]
The method according to [25] or [26], wherein the median size (X50) of the first granules is 130 μm to 240 μm, and the median size (X50) of the second granules is 170 μm to 240 μm.
[29]
The method according to [25] to [28], wherein the granular preparation is granules for an oral suspension or a dry syrup.
[30]
The method according to [29], wherein the granular preparation is granules for an oral suspension.
[31]
The method according to [29], wherein the granular preparation is a dry syrup.
[32]
A granular preparation comprising
(A) edoxaban or a pharmacologically acceptable salt thereof,
(B) a sugar alcohol,
(C) a water-swelling additive,
(D) 0.5 to 10% by weight of carmellose sodium with respect to the total weight of the preparation, and
(E) 70 to 90% by weight of xylitol or sorbitol with respect to the total weight of the preparation.

Advantageous Effects of Invention

The present invention provides a granular preparation that contains edoxaban or a pharmacologically acceptable salt thereof, is rapidly dissolved or suspended by the addition of water, has excellent dissolution properties, and reduces the bitterness of the active ingredient. The present invention further provides a granular preparation containing edoxaban or a pharmacologically acceptable salt thereof and is excellent in terms of uniformity of dosage units without segregation when two types of granules, i.e., drug-containing granules and drug-free granules, are mixed, and a method for producing the same. Furthermore, the present invention provides a method for producing a granular preparation containing edoxaban or a pharmacologically acceptable salt thereof and having excellent properties as described above using a conventional facility without the need for complicated operations. Further, the present invention provides a granular preparation containing edoxaban or a pharmacologically acceptable salt thereof and a high content of xylitol or sorbitol, having good manufacturability, and having no reduction in content of the active ingredient after production, and a method for producing the same.

DESCRIPTION OF EMBODIMENTS

Figure 1:
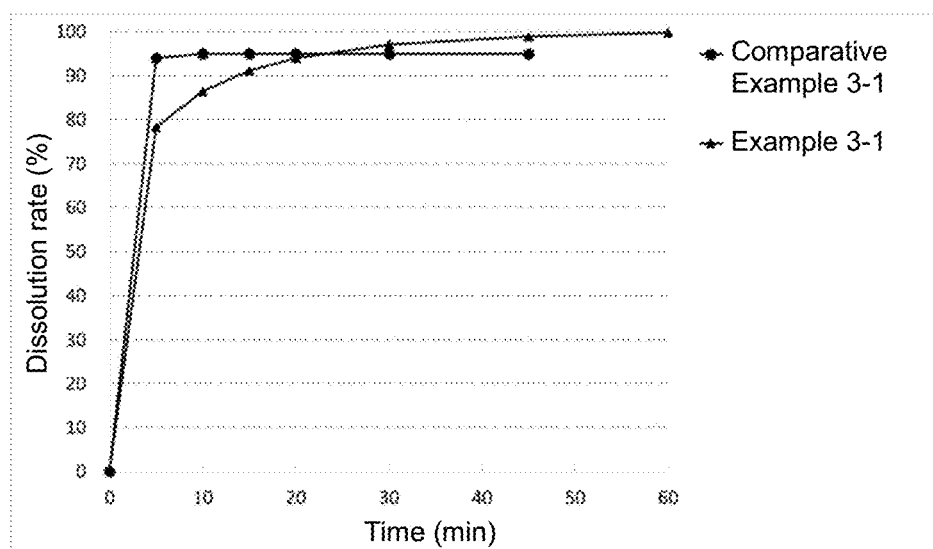
FIG. 1 is a graph showing the dissolution rate of edoxaban in a pH 6.0 phosphate buffer solution for the granular preparations of Comparative Examples 3-1 (one-granule method) and Example 3-1 (two-granule method) produced by a fluidized-bed granulation method. In the drawing, the ordinate depicts the dissolution rate (%), and the abscissa depicts time (min).

In the present specification, the granular preparation for an oral suspension preparation is a granular preparation that becomes a suspension preparation for oral administration when water is added thereto and is a preparation usually suspended in use. The granular preparation for an oral suspension preparation can also be administered, once suspended, using a suitable administration device (for example, an oral syringe). The definition of granular preparations for an oral suspension preparation conforms to the definition described in The European Pharmacopoeia 9th edition, in powders and granules for oral solutions and suspensions.

In the present specification, the dry syrup is a preparation in a granular form that becomes a solution or a suspension when water is added thereto and is usually a preparation dissolved or suspended in use. The dry syrup can also be administered, once dissolved or suspended, using a suitable administration device (for example, an oral syringe). The definition of dry syrups conforms to the definition described in The Japanese Pharmacopoeia 17th edition.

In the present specification, the total weight of the preparation in the case of a preparation containing first granules and second granules refers to the total weight of the preparation based on the sum of the weights of the first granules, the second granules and other additives.

The term "X50" according to the present invention refers to a 50% cumulative particle size measured by a sieving method. In the present specification, X50 is also referred to as a median size.

The degree of sweetness of the sweetener according to the present invention is a relative value that indicates the sweet taste intensity of each sweetener when the sweet taste of sucrose is defined as 1.0. In general, the degree of sweetness can be determined by sensory testing in humans which involves comparing a given concentration of a sucrose solution with the concentration of each sweetener that exhibits the same intensity of sweetness as that of the sucrose solution.

The term "$R_2/R_1$" according to the present invention refers to the ratio of the median size ($R_2$) of the second granules to the median size ($R_1$) of the first granules.

Edoxaban used in the present invention is $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

[Formula 2]

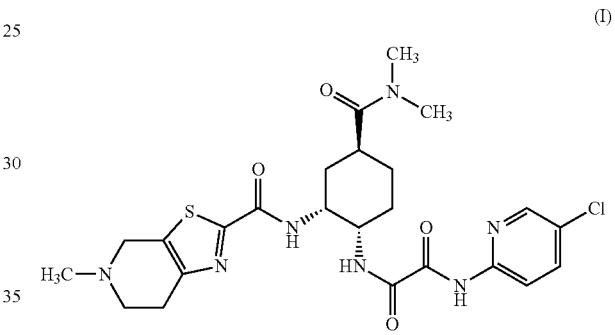

(hereinafter, also referred to as compound I).

Compound I may be a pharmacologically acceptable salt. The pharmacologically acceptable salt thereof also includes a solvate (including a hydrate). Examples of the salt of compound I preferably include $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonic acid monohydrate (edoxaban tosylate hydrate) represented by the following formula (Ia):

[Formula 3]

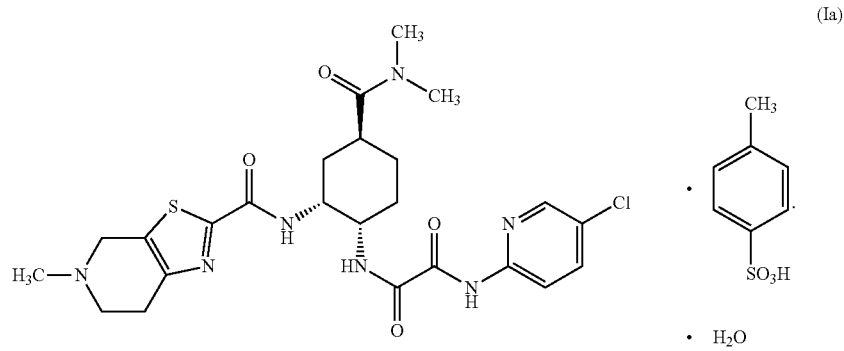

Edoxaban or a pharmacologically acceptable salt thereof exerts an antithrombotic effect by selectively, reversibly and directly inhibiting activated blood coagulation factor X (FXa), which has the effect of forming a thrombus by converting prothrombin to thrombin and promoting fibrin formation in the blood coagulation cascade.

Edoxaban or a pharmacologically acceptable salt thereof has been used in clinical trials carried out in Japan and overseas for the suppression of occurrence of venous thromboembolism in patients undergoing lower limb orthopedic surgery including total knee replacement, total hip replacement, or hip fracture surgery, for the suppression of occurrence of ischemic stroke and systemic embolism in non-valvular atrial fibrillation patients, and for the treatment and the suppression of recurrence of venous thromboembolism (deep venous thromboembolism and pulmonary thromboembolism).

Edoxaban or a pharmacologically acceptable salt thereof is usually orally administered once a day at a dose, in terms of edoxaban, of 30 mg (for a body weight of 60 kg or lower) or 60 mg (for a body weight exceeding 60 kg) to an adult for the suppression of occurrence of ischemic stroke and systemic embolism in non-valvular atrial fibrillation patients, and for the treatment and the suppression of recurrence of venous thromboembolism (deep venous thromboembolism and pulmonary thromboembolism). The dose may be decreased to 30 mg once a day according to renal function or concomitant drugs. Also, edoxaban or a pharmacologically acceptable salt thereof is usually orally administered once a day at a dose, in terms of edoxaban, of 30 mg to an adult for the suppression of occurrence of venous thromboembolism in patients undergoing lower limb orthopedic surgery.

The content of edoxaban or a pharmacologically acceptable salt thereof contained in the granular preparations of the present invention is not particularly limited as long as the effects of the present invention are not impaired. The content is preferably 0.3 to 10% by weight, more preferably 0.3 to 5% by weight, still more preferably 0.3 to 3% by weight, with respect to the total weight of the preparation.

Examples of the sugar alcohol (B) according to the present invention include D-mannitol, xylitol, erythritol, maltitol, and sorbitol, and these can be blended singly or in combinations of two or more thereof. Examples of the sugar alcohol (B) preferably include D-mannitol, xylitol, and erythritol, more preferably D-mannitol. D-mannitol that can usually be used conforms to the Japanese, European and U.S. Pharmacopoeia.

The content of the sugar alcohol (B) is not particularly limited as long as the effects of the present invention are not impaired and is usually 3 to 15% by weight, preferably 3 to 10% by weight, with respect to the total weight of the preparation.

The water-swelling additive (C) according to the present invention means a pharmaceutical additive that swells by the addition of water. Examples of the water-swelling additive (C) according to the present invention include excipients and bases having water swellability. Specific examples of the water-swelling additive include pregelatinized starch, crystalline cellulose, sodium carboxymethyl starch, carmellose (carboxymethylcellulose), carmellose calcium, croscarmellose sodium (croscarboxymethylcellulose sodium), soybean lecithin, low-substituted hydroxypropylcellulose, tragacanth powder, and bentonite. These water-swelling additives can be blended singly or in combinations of two or more thereof. Among these water-swelling additives (C), pregelatinized starch and/or crystalline cellulose is preferred, and pregelatinized starch is more preferred.

The content of the water-swelling additive (C) according to the present invention is not particularly limited as long as the effects of the present invention are not impaired and is usually 1 to 10% by weight, preferably 1 to 5% by weight, with respect to the total weight of the preparation.

The blending ratio between the water-swelling additive (C) and the sugar alcohol (B) according to the present invention is not particularly limited as long as the effects of the present invention are not impaired and is 1 to 10 parts by weight, preferably 1.5 to 4 parts by weight, of the sugar alcohol (B) with respect to 1 part by weight of the water-swelling additive (C).

Examples of the disintegrant include adipic acid, alginic acid, pregelatinized starch, sodium carboxymethyl starch, carmellose, carmellose calcium, carmellose sodium (hereinafter, also referred to as CMC-Na), aqueous silicon dioxide, calcium citrate, croscarmellose sodium, crospovidone, light anhydrous silicic acid, crystalline cellulose, synthetic aluminum silicate, wheat starch, rice starch, cellulose acetate phthalate, calcium stearate, low-substituted hydroxypropylcellulose, corn starch, tragacanth powder, potato starch, hydroxyethylmethylcellulose, hydroxypropyl starch, pregelatinized starch, monosodium fumarate, povidone, citric anhydride, methylcellulose, and calcium dihydrogen phosphate. These can be blended singly or in combinations of two or more thereof. The disintegrant is preferably crospovidone and/or sodium carboxymethyl starch, more preferably crospovidone.

The content of the disintegrant is not particularly limited as long as the effects of the present invention are not impaired and is preferably 0.1 to 10% by weight, more preferably 0.1 to 5% by weight, still more preferably 0.3 to 3% by weight, with respect to the total weight of the preparation.

Examples of the binder include gum arabic, sodium alginate, carboxyvinyl polymer, gelatin, dextrin, pectin, sodium polyacrylate, pullulan, methylcellulose, hydroxypropylcellulose, hydroxypropylmethylcellulose, polyvinyl alcohol, polyvinylpyrrolidone and Macrogol and these can be blended singly or in combinations of two or more thereof. The binder is preferably hydroxypropylcellulose.

The content of the binder is not particularly limited as long as the effects of the present invention are not impaired and is preferably 0.1 to 5% by weight, more preferably 0.1 to 3% by weight, still more preferably 0.1 to 1% by weight, with respect to the total weight of the preparation.

A product conforming to the Japanese, European or U.S. Pharmacopoeia can usually be used as the carmellose sodium contained in the granular preparations of the present invention. The carmellose sodium exhibits moderate viscosity upon addition of water and can therefore be expected to play a role in facilitating the suspension of a drug. In the present invention, the carmellose sodium exerts an effect of facilitating the suspension of the drug together with the xylitol or the sorbitol. The content of carmellose as the component (D) is not particularly limited as long as the effects of the present invention are not impaired and is preferably 0.5 to 10% by weight, more preferably 0.5 to 5% by weight, still more preferably 1 to 5% by weight, with respect to the total weight of the preparation.

A product conforming to the Japanese, European or U.S. Pharmacopoeia can usually be used as the xylitol or the sorbitol in the granular preparation of the present invention. The xylitol or the sorbitol not only functions as a sweetener that reduces the bitterness of the active ingredient by its sweetness but also exhibits moderate viscosity upon addition of water and can therefore be expected to play a role in facilitating the suspension of the drug. The content of the xylitol or the sorbitol as the component (E) is not particularly limited as long as the effects of the present invention are not impaired and is preferably 70 to 90% by weight, more preferably 80 to 90% by weight, with respect to the total weight of the preparation.

The granular preparations of the present invention can contain various additives generally used in the production of preparations, in addition to those described above, as long as the effects of the present invention are not hindered.

Examples of the additives can include excipients, binders, lubricants, coating agents, plasticizers, coloring agents, flavoring agents, sweeteners, corrigents, fluidizers, foaming agents and surfactants.

Examples of the excipient can include organic excipients selected from sugars, sugar alcohols, starches, and celluloses, and inorganic excipients. Examples of the sugar can include one or a combination of two or more selected from lactose, sucrose, fructooligosaccharide, glucose, palatinose, maltose, hydrogenated maltose starch, powder sugar, maltose syrup powder, fructose, lactulose and honey. Examples of the sugar alcohol include D-mannitol, xylitol, erythritol, maltitol, and sorbitol. Examples of the starch can include one or a combination of two or more selected from corn starch, potato starch, rice starch, and pregelatinized starch. Examples of the cellulose can include crystalline cellulose as well as one or a combination of two or more selected from powdered cellulose, hydroxypropylcellulose, carmellose, carmellose calcium and croscarmellose sodium. Examples of the inorganic excipient can include one or a combination of two or more selected from synthetic hydrotalcite, precipitated calcium carbonate, aqueous silicon dioxide, light anhydrous silicic acid, magnesium aluminosilicate and magnesium hydroxide.

Examples of the binder can include one or a combination of two or more selected from gum arabic, sodium alginate, carboxyvinyl polymer, gelatin, dextrin, pectin, sodium polyacrylate, pullulan, methylcellulose, hydroxypropylcellulose, hydroxypropylmethylcellulose, polyvinyl alcohol, polyvinylpyrrolidone and Macrogol.

Examples of the lubricant include one or a combination of two or more selected from magnesium stearate, calcium stearate, sodium stearyl fumarate and talc.

Examples of the coating agent that covers the surface of a drug in a powdery form (the surface of crystals) or the granule surface of a granulated drug can include one or a combination of two or more selected from: cellulose derivatives such as hypromellose (hydroxypropylmethylcellulose), hydroxypropylcellulose, ethylcellulose, and methylcellulose; polyvinyl compounds such as polyvinyl alcohol, povidone (polyvinylpyrrolidone), polyvinylacetal diethylaminoacetate, and vinyl acetate resin; acrylic acid derivatives such as amino alkyl methacrylate copolymer RS and ethyl acrylate-methyl methacrylate copolymer dispersions; and sugars (including sugar alcohols) such as saccharose and mannitol for use in sugar coating.

Examples of the plasticizer that is combined with the coating agent can include one or a combination of two or more selected from diethyl sebacate, dibutyl sebacate, triethyl citrate, stearic acid, polyethylene glycol and triacetin.

Examples of the coloring agent can include one or a combination of two or more selected from food dyes such as food yellow No. 5, food red No. 2, and food blue No. 2, food lake dyes, yellow iron sesquioxide, iron sesquioxide, titanium oxide, β-carotene, and riboflavin.

Examples of the flavoring agent can include one or a combination of two or more selected from orange, lemon, strawberry, mint, menthol, Menthol Micron and various fragrances.

Examples of the sweetener can include one or a combination of two or more selected from saccharine sodium, saccharine, aspartame, acesulfame potassium, dipotassium glycyrrhizinate, sucralose, stevia and thaumatin.

Examples of the corrigent can include one or a combination of two or more selected from sodium chloride, magnesium chloride, disodium inosinate, sodium L-glutamate and honey.

Examples of the fluidizer can include one or a combination of two or more selected from aqueous silicon dioxide, light anhydrous silicic acid and talc.

Examples of the foaming agent can include tartaric acid and/or anhydrous citric acid.

Examples of the surfactant can include one or a combination of two or more selected from polyoxyl 40 stearate, sorbitan fatty acid ester, polyoxyethylene hydrogenated castor oil, polysorbate, glycerin monostearate and sodium lauryl sulfate.

Hereinafter, the method for producing the granular preparation of the present invention will be described.

The method for producing the granular preparation of the present invention can be carried out by a production method described below.

The following two-granule method (b) is preferably adopted in the production of the granular preparation of the present invention.

(a) Method for producing granular preparation by one-granule method (A) Edoxaban or a pharmacologically acceptable salt thereof, (B) a sugar alcohol, (C) a water-swelling additive, (D) 0.5 to 10% by weight of carmellose sodium with respect to the total weight of the preparation, (E) 70 to 90% by weight of xylitol with respect to the total weight of the preparation, and other additives, etc. are wet-granulated using water, or an aqueous solution or dispersion of the binder. A mixing-stirring granulation method, a high-speed stirring granulation method, a fluidized-bed granulation method, a tumbling granulation method, or the like generally used can be used as the wet granulation method. A high-speed stirring granulation method or a fluidized-bed granulation method is preferred, and a fluidized-bed granulation method is more preferred.

(b) Method for producing granular preparation by two-granule method

1. Step of Producing First Granule (Drug-Containing Granule)

(A) Edoxaban or a pharmacologically acceptable salt thereof, (B) a sugar alcohol, (C) a water-swelling additive, and other additives, etc. are wet-granulated using water, or an aqueous solution or dispersion of the binder. A mixing-stirring granulation method, a high-speed stirring granulation method, a fluidized-bed granulation method, a tumbling granulation method, or the like generally used can be used as the wet granulation method. A high-speed stirring granulation method or a fluidized-bed granulation method is preferred, and a fluidized-bed granulation method is more preferred.

The obtained first granules may be subjected to drying and/or particle size selection, if necessary. The particle size of the first granules is not particularly limited as long as the effects of the present invention are not impaired and preferably the median size (X50) thereof is 130 μm to 240 μm, more preferably 130 to 220 μm.

2. Step of Producing Second Granule (Drug-Free Granule)

(D) 0.5 to 10% by weight of carmellose sodium with respect to the total weight of the preparation, and (E) 70 to 90% by weight of xylitol with respect to the total weight of the preparation are wet-granulated using water. In another aspect, a portion or the whole of the carmellose sodium (D) is dissolved or dispersed in water, and the wet granulation may be performed by use of the solution or the dispersion. A mixing-stirring granulation method, a high-speed stirring granulation method, a fluidized-bed granulation method, a tumbling granulation method, or the like generally used can be used as the wet granulation method. A high-speed stirring granulation method or a fluidized-bed granulation method is preferred, and a fluidized-bed granulation method is more preferred.

The obtained second granules may be subjected to drying and/or particle size selection, if necessary. The particle size of the second granules is not particularly limited as long as the effects of the present invention are not impaired and the median size (X50) thereof is preferably 170 μm to 240 μm.

3. Step of Mixing First Granules and Second Granules

The obtained first granules and second granules are mixed to obtain the granular preparations of the present invention. When the obtained first granules and second granules are mixed, the ratio ($R_2/R_1$) of the median size ($R_2$) of the second granules to the median size ($R_1$) of the first granules is selected so as not to cause the segregation of these two types of granules. The median size ratio ($R_2/R_1$) is preferably 0.75 to 1.75, more preferably 0.85 to 1.70. A stirring mixer or a V-shaped mixer generally used can be used in the mixing.

A feature of the granular preparation of the present invention obtained through the steps described above is that the granular preparation is rapidly dissolved or suspended by the addition of water and reduces the bitterness of the active ingredient. The granular preparation of the present invention further has a feature of being excellent in terms of uniformity of dosage units and the dissolution properties of the active ingredient, without the segregation of the two types of granules mixed. In addition to these features, the granular preparations of the present invention can be produced using a conventional facility without the need for complicated operations.

The dissolution properties of the granular preparations of the present invention can be evaluated by a dissolution test method described in, for example, the Japanese Pharmacopoeia, the U.S. Pharmacopoeia (USP) and the European Pharmacopoeia. When the granular preparation of the present invention is subjected to a dissolution test by a method described in the European Pharmacopeia (paddle method: 50 rpm), the average dissolution rate of edoxaban in a dissolution test medium of pH 6.0 is 70% or higher in 45 minutes after the start of the dissolution test, preferably 75% or higher in 45 minutes after the start of the dissolution test, more preferably 80% or higher in 45 minutes after the start of the dissolution test.

The uniformity of dosage units of the granular preparation of the present invention can be evaluated according to a content uniformity test among the methods for testing uniformity of dosage units specified by the Japanese, U.S., and European Pharmacopoeia. Specifically, the content of edoxaban in preparations is measured by HPLC for 10 or 30 bottles packed with the granular preparations of the present invention, and an acceptance value (AV) is calculated according to the expression (a) given below. When AV is 15.0% or less (for 10 samples) or 25.0% or less (for 30 samples), the preparations are confirmed to have a uniform content.

[Expression 1]

Acceptance value (AV) of content uniformity (%) = $|M - \overline{X}| + ks$  (a)

$\overline{X}$: Content in preparation (%)

$k$: 2.0 (when the number of samples is 30),
2.4 (when the number of samples is 10)

$M: \begin{cases} 98.5\% & (\overline{X} < 98.5\%) \\ \overline{X} & (98.5\% \leq \overline{X} \leq 101.5\%) \\ 101.5\% & (101.5\% < \overline{X}) \end{cases}$ $s$: Standard deviation $\sqrt{\dfrac{\sum_{i=1}^{n}(x_i - \overline{X})^2}{n-1}}$ ($n$ = the number of samples, $x_1, x_2, \ldots x_n$ represent the contents of the active ingredient contained in individual samples tested)

An aqueous solution or suspension of the granular preparation of the present invention may be prepared by the addition of water, and this aqueous solution or suspension can be administered to a patient by oral administration (a device such as an oral syringe may be used). The granular preparation of the present invention provides a preparation that can be conveniently taken not only by general patients but by elderly or child patients having difficulty in swallowing.

Next, the present invention will be described in detail with reference to Examples. However, the present invention is not limited by these examples by any means.

EXAMPLES

In the present Examples, measurement by high-performance liquid chromatography (hereinafter, also referred to as HPLC) was performed under the following conditions:
HPLC measurement conditions
Column: AGILENT Poroshell 120 EC C18 (2.7 μm, 50×4.6 mm)
Temperature: 40° C.
Mobile phase: solution A—pH 4.5 acetate buffer solution/acetonitrile (9/1 (v/v))
solution B—pH 4.5 acetate buffer solution/acetonitrile (2/8 (v/v))
Solution A:solution B=74:26
Flow rate: 1 mL/min
Detection wavelength: 290 nm
Injection volume: 5 μL (injected at 10° C.)

(Example 1) Study of Sweetener and Stability Evaluation of Suspension

A sensory test and evaluation of suspension stability were conducted using sucralose, xylitol, or sorbitol as a sweetener. The content of the sweetener was set with reference to the degree of sweetness (sucralose: 600, xylitol: 1, sorbitol: 0.8) such that the sweetness was at the same level among preparations.
(1) Method for Producing Granular Preparation A fluidized-bed granulation dryer (S2-B5-F2, Aeromatic Fielder AG) was charged with edoxaban tosylate hydrate, D-mannitol, pregelatinized starch, crospovidone, the sweetener, and carmellose sodium according to the weight ratio of the formulation described in Table 1-1. The mixture was granulated by spraying a liquid of hydroxypropylcellulose and strawberry flavor dissolved in purified water, and then dried to obtain the granular preparations of Comparative Examples 1-1 and 1-2 and Examples 1-1 to 1-3.
(2) Evaluation Method Sensory evaluation: The granular preparations of Comparative Examples 1-1 and 1-2 and Examples 1-1 to 1-3 produced by the method described above were administered to humans and evaluated for their taste and satisfaction levels immediately after the administration and 2 to 5 minutes after the administration on a scale of 1 to 5 (1: dislike very much, 2: dislike, 3: neither like nor dislike, 4: like, 5: like very much). As a result of the evaluation, a sample that got a score exceeding 4 as the average value was described by a circle, and a sample that got a score below 4 as the average value was described by an X-mark, in Table 1-2.

Evaluation of suspension stability: Edoxaban tosylate hydrate, D-mannitol, pregelatinized starch, crospovidone, hydroxypropylcellulose, the sweetener, CMC-Na, and strawberry flavor were weighed into a 25 mL amber glass vial (Code: 0755, Gerresheimer AG) according to the formulation described in Table 1-1, and then mixed. Water was added so as to attain 6 mg/mL as the theoretical content of edoxaban. The mixture was shaken to prepare a suspension, and 1 mL of a sample was harvested from a position of 1 cm from the liquid level of the suspension immediately, 5 minutes, 15 minutes, and 30 minutes after the suspension was prepared, and the concentration of edoxaban was evaluated by HPLC (AGILENT 1100, 1200, or 1260; Agilent Technologies, Inc.). A sample having a time-dependent change in concentration within the range of 90% to 110% at all the points in time of the evaluation was described by a circle, and a sample having a time-dependent change outside the range described above was described by an X-mark, in Table 1-2.
(3) Results The results of the sensory evaluation and evaluation of suspension stability are shown in Table 1-2. As a result of the sensory evaluation, the taste of preparations produced using xylitol or sorbitol as a sweetener as in Examples 1-1 to 1-3 were found to not hinder the preparations from being taken. The granular preparations of Examples 1-1 to 1-3 were also found to have a change in the concentration of edoxaban in the suspension within the range of 90% to 110%. These results demonstrated that a granular preparation adopting CMC-Na and xylitol or sorbitol in combination offers a highly stable suspension and has performance suitable as the granular preparations of the present invention.

TABLE 1-2

| Comparative Example/ Example | Comparative Example 1-1 | Comparative Example 1-2 | Example 1-1 | Example 1-2 | Example 1-3 |
| --- | --- | --- | --- | --- | --- |
| Sensory evaluation | ○ | x | ○ | ○ | ○ |
| Evaluation of suspension stability | x | ○ | ○ | ○ | ○ |

(Example 2) Study on Production Method

A study was carried out on methods for producing the granular preparations of the present invention by the one-granule method and the two-granule method described below.
(1) Method for Producing Granular Preparation by One-Granule Method Granular preparations of Comparative Examples 2-1 to 2-5 were produced in the same way as in Example 1 according to the weight ratio of the formulation described in Table 2-1.
(2) Method for Producing Granular Preparation by Two-Granule Method Production of first granule (drug-containing granule): A fluidized-bed granulation dryer (S2-B5-F2, Aeromatic Fielder AG) was charged with edoxaban tosylate hydrate, D-mannitol, pregelatinized starch, and crospovidone according to the weight ratio of the formulation described in Table 2-1. A liquid of hydroxypropylcellulose dissolved in purified water was sprayed thereon, and then dried to obtain first granules (drug-containing granules).

Production of second granule (drug-free granule): A fluidized-bed granulation dryer (S2-B5-F2, Aeromatic Fielder AG) was charged with xylitol and approximately 90% of the whole amount of CMC-Na according to the weight ratio of the formulation described in Table 2-1. A liquid of the remaining amount of CMC-Na and strawberry flavor dissolved in purified water was sprayed thereon, and then dried to obtain second granules (drug-free granules).

Mixing of two types of granules: A tumble mixer (Limitec GmbH) was charged with a weight ratio of 14.4% by weight of the first granules and 85.6% by weight of the second granules, which were then mixed for 15 minutes to obtain the granular preparations of Examples 2-1 to 2-4 shown in Table 2-3.

TABLE 1-1

| Comparative Example/Example | Comparative Example 1-1 | Comparative Example 1-2 | Example 1-1 | Example 1-2 | Example 1-3 |
| --- | --- | --- | --- | --- | --- |
| Edoxaban tosylate hydrate | 161.6 | 161.6 | 161.6 | 161.6 | 161.6 |
| D-Mannitol | 396.8 | 396.8 | 396.8 | 396.8 | 396.8 |
| Pregelatinized starch | 168.0 | 168.0 | 168.0 | 168.0 | 168.0 |
| Crospovidone | 42.8 | 42.8 | 42.8 | 42.8 | 42.8 |
| Hydroxypropylcellulose | 24.4 | 24.4 | 24.4 | 24.4 | 24.4 |
| Sweeteners   Sucralose | 7.5 | 3.8 | — | — | — |
| Xylitol | — | — | 4500.0 | — | 4500.0 |
| Sorbitol | — | — | — | 7500.0 | — |
| CMC-Na | 75.0 | 200.0 | 200.0 | 200.0 | 160.0 |
| Strawberry flavor | 1.0 | 1.0 | 1.0 | 1.0 | 1.0 |
| Total amount of granules | 877.1 | 998.4 | 5494.6 | 8494.6 | 5454.6 |

*All the weights of the components are expressed in units of mg.

(3) Evaluation Method

The granular preparations of Comparative Examples 2-1 to 2-5 and Examples 2-1 to 2-4 obtained by the methods described above were each weighed into a volumetric flask, diluted with a mixed solvent of acetonitrile and water (3:7 (v/v)), and completely dissolved by shaking and ultrasonication. An aliquot was harvested from the obtained solution and diluted so as to contain 80.8 μg/mL of edoxaban tosylate hydrate as a theoretical amount to prepare a solution for evaluation. Aside from this, a standard solution of edoxaban tosylate hydrate was prepared, and the content of edoxaban tosylate hydrate in the solution for evaluation was measured by use of HPLC to calculate the ratio of the actual content to the theoretical content (content %).

(4) Results

The results of measuring the content of edoxaban in the granular preparations produced according to the production methods based on the one-granule method and the two-granule method are shown in Tables 2-2 and 2-3. As a result, the granular preparations of Comparative Examples 2-1 to 2-5 produced by the one-granule method were found to have a reduced content of edoxaban. This content reduction suggests a possible characteristic that, in the one-granule method, xylitol, which constitutes the major part of the raw materials, takes up moisture during the granulation step so that a portion thereof adheres, together with the active ingredient, to wall surfaces and the bag filter. On the other hand, the two-granule method solved this problem by separately using hygroscopic xylitol and the active ingredient edoxaban in production and thereby suppressing the adherence of the active ingredient to the inside of the production equipment. In other words, the granular preparations of Examples 2-1 to 2-4 produced by the two-granule method were found to not reduce the content of edoxaban.

TABLE 2-1

| Components blended | Formulation (mg) |
| --- | --- |
| Edoxaban tosylate hydrate | 80.8 |
| D-mannitol | 198.4 |
| Pregelatinized starch | 84.0 |
| Crospovidone | 21.4 |
| Hydroxypropylcellulose | 12.2 |
| CMC-Na | 100.0 |
| Xylitol | 2250.0 |
| Strawberry flavor | 0.5 |
| Total amount of granules | 2747.3 |

TABLE 2-2

| Comparative Example/Example | Comparative Example 2-1 | Comparative Example 2-2 | Comparative Example 2-3 | Comparative Example 2-4 | Comparative Example 2-5 |
| --- | --- | --- | --- | --- | --- |
| Production method | One-granule method | | | | |
| Content of edoxaban (%) | 90.6 | 94.4 | 97.2 | 91.2 | 88.8 |

TABLE 2-3

| Comparative Example/Example | Example 2-1 | Example 2-2 | Example 2-3 | Example 2-4 |
| --- | --- | --- | --- | --- |
| Production method | Two-granule method | | | |
| Content of edoxaban (%) | 100.5 | 101.0 | 98.4 | 98.1 |

(Example 3) Comparison of Dissolution Performance Between Granular Preparations Produced by One-Granule Method and Two-Granule Method The dissolution performance of granular preparations differing in production method was compared by a dissolution test between granular preparations produced by the one-granule method and the two-granule method described above.

(1) Method for Producing Granular Preparation

The granular preparations of Comparative Examples 3-1 (one-granule method) and Example 3-1 (two-granule method) were produced according to the method for producing a granular preparation by the one-granule method described in Example 2(1), the method for producing a granular preparation by the two-granule method described in Example 2(2), and the weight ratio of the formulation described in Table 2-1.

(2) Evaluation Method

Dissolution Test Method

A dissolution test was conducted according to the method described in the European Pharmacopoeia (paddle method: 50 rpm) using a phosphate buffer solution of pH 6.0.

(3) Results

FIG. 1 shows the dissolution test results for the granular preparation of Comparative Example 3-1 produced by the one-granule method and the granular preparation of Example 3-1 produced by the two-granule method. The granular preparation produced by the one-granule method demonstrated high dissolution properties but, as evident from the results of Example 2, had reduced content of edoxaban and thereby failed to have a dissolution rate of 100% (in other words, the content of edoxaban did not reach the theoretical content). On the other hand, the granular preparation produced by the two-granule method demonstrated high dissolution properties and also did not reduce the content of edoxaban and was thereby revealed to be an excellent preparation.

(Example 4) Study on Mixing Conditions for First Granule and Second Granule in Two-Granule Method A study was carried out on the particle sizes of the first granules and the second granules to search for conditions for granular preparations without causing segregation.

(1) Production Method

First granules and second granules were produced according to the production method based on the two-granule method described in Example 2(2) and the weight ratio of the formulation described in Table 2-1. Then, a particle size selection operation was performed using a particle size selector (QC-197s, Quadro Comil, Quadro Engineering Corp.) to obtain granules having a median size (X50) of 137, 177, or 212 µm for the first granules, and granules having a median size (X50) of 179, 181, or 234 µm for the second granules. The particle size distributions of the first granules and the second granules were measured by the sieving method using a sieving shaker (AS200, manufactured by Retsch GmbH), and their 50% cumulative particle sizes (X50; median size) were calculated.

Next, an experiment was conducted to study mixing conditions for the first granules and the second granules according to the combinations of the particle sizes of the first granules and the second granules described in Table 4-1 on a scale of about 10 kg as the total amount of the granular preparation. A bottle-type mixer (manufactured by Limitec GmbH) was charged with the granules obtained by the method described above such that the proportion of the first granules was 14.4% by weight and the proportion of the second granules was 85.6% by weight, and these granules were mixed at 6 rpm for 20 minutes to produce the granular preparations of Examples 4-1 to 4-3.

(2) Evaluation Method

Mixing Uniformity

Figure 2:
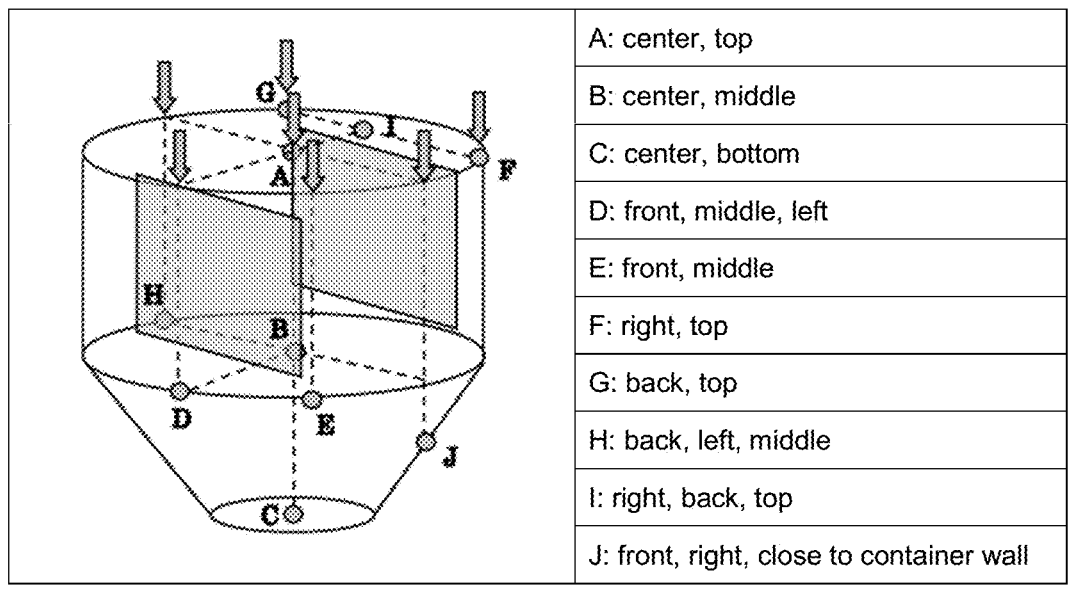
FIG. 2 is a schematic diagram of a bottle-type mixer for use in the mixing of first granules and second granules. In the drawing, A to J denote the positions of sampling for evaluating mixing uniformity in Examples 4-1 to 4-3.

A sample was harvested from sampling positions A to J shown in the schematic diagram of FIG. 2, 10 minutes, 15 minutes, and 20 minutes after the start of mixing in the bottle-type mixer in the production method described in Example 4(1). The content of edoxaban in the obtained samples was measured in the same way as in Example 2(3), and a mean and standard deviation thereof were calculated to evaluate mixing uniformity.

Uniformity of Dosage Units

Each bottle was filled with 2.75 g (80.8 mg as a theoretical amount of edoxaban tosylate hydrate) of the granular preparation produced by the method described in Example 4(1), using a bottle filling machine (SW703, Collischan GmbH). The ratio of the actual content to the theoretical content of edoxaban per bottle (content %) was measured for 10 samples harvested in chronological order during the bottle filling step. The measurement was performed in the same way as in Example 2(3), and a mean and standard deviation of the content were calculated. An acceptance value was calculated according to the European Pharmacopoeia to evaluate uniformity of dosage units.

(3) Results

The results of mixing uniformity and uniformity of dosage units are shown in Table 4-1 for the granular preparations of Examples 4-1 to 4-3 produced using varying combinations of particle sizes of the first granules and the second granules. A feature of the granular preparation of Example 4-1 was that X50 of the first granules was larger than that of the second granules. A feature of the granular preparation of Example 4-2 was that X50 of the first granules was almost the same size as X50 of the second granules. A feature of the granular preparation of Example 4-3 was that X50 of the first granules was smaller than that of the second granules. In Examples 4-1 to 4-3, variations in the standard deviation values at 10 minutes, 15 minutes, and 20 minutes were seen, suggesting that there existed variations ascribable to sampling after uniformity reached a steady state. The magnitudes of the standard deviation values of the uniformity of dosage units and the mixing uniformity at the completion of mixing (20 minutes after the start of mixing) in Examples 4-1 to 4-3 were in the same order (Example 4-2<Example 4-3<Example 4-1). However, when the values were compared, the values of uniformity of dosage units were smaller than the values of mixing uniformity. The acceptance values of uniformity of dosage units in Examples 4-1 to 4-3 were smaller than L1 (15%), which is a criterion of the European Pharmacopoeia and was found to be satisfied.

The results described above demonstrated that a granular preparation that satisfies the criteria required by the regulatory authority of each country can be produced on a scale of about 10 kg according to the present invention.

TABLE 4-1

| Example | | Example 4-1 | Example 4-2 | Example 4-3 |
|---|---|---|---|---|
| X50 (µm) | First granule ($R_1$) | 212 | 177 | 137 |
| | Second granule ($R_2$) | 181 | 179 | 234 |
| | $R_2/R_1$ | 0.85 | 1.01 | 1.71 |
| Mixing uniformity (n = 10) 10 minutes | | | | |
| Mean (%) | | 98.0 | 99.1 | 92.3 |
| Standard deviation | | 3.3 | 1.9 | 8.2 |
| 15 minutes | | | | |
| Mean (%) | | 96.9 | 98.4 | 94.2 |
| Standard deviation | | 2.9 | 2.5 | 3.9 |
| 20 minutes | | | | |
| Mean (%) | | 96.2 | 98.4 | 94.1 |
| Standard deviation | | 5.8 | 2.0 | 4.7 |
| Uniformity of dosage units (n = 10) | | | | |
| Mean (%) | | 100.9 | 97.5 | 94.4 |
| Standard deviation | | 4.7 | 1.5 | 2.5 |
| Acceptance value (%) | | 11.2 | 4.7 | 10.2 |

The invention claimed is:

1. A granular preparation comprising
   first granules containing
   (A) edoxaban or a pharmacologically acceptable salt thereof,
   (B) a sugar alcohol, and
   (C) a water-swelling additive, and
   second granules containing
   (D) 0.5 to 10% by weight of carmellose sodium with respect to the total weight of the preparation, and
   (E) 70 to 90% by weight of xylitol or sorbitol with respect to the total weight of the preparation.

2. The granular preparation according to claim 1, wherein the ratio ($R_2/R_1$) of the median size of the second granules ($R_2$) to the median size of the first granules ($R_1$) is 0.75 to 1.75.

3. The granular preparation according to claim 1, wherein the median size (X50) of the first granules is 130 µm to 240 µm, and the median size (X50) of the second granules is 170 µm to 240 µm.

4. The granular preparation according to claim 1, wherein the granular preparation comprises 0.3 to 10% by weight of edoxaban or a pharmacologically acceptable salt thereof (A) with respect to the total weight of the preparation.

5. The granular preparation according to claim 1, wherein edoxaban or a pharmacologically acceptable salt thereof (A) is edoxaban tosylate monohydrate.

6. The granular preparation according to claim 1, wherein the sugar alcohol (B) is D-mannitol, xylitol, or erythritol.

7. The granular preparation according to claim 6, wherein the sugar alcohol (B) is D-mannitol.

8. The granular preparation according to claim 1, wherein the granular preparation comprises 3 to 15% by weight of the sugar alcohol (B) with respect to the total weight of the preparation.

9. The granular preparation according to claim 1, wherein the water-swelling additive (C) is pregelatinized starch and/or crystalline cellulose.

10. The granular preparation according to claim 9, wherein the water-swelling additive (C) is pregelatinized starch.

11. The granular preparation according to claim 1, wherein the granular preparation comprises 1 to 10% by weight of the water-swelling additive (C) with respect to the total weight of the preparation.

12. The granular preparation according to claim 1, further comprising a disintegrant.

13. The granular preparation according to claim 12, wherein the disintegrant is contained in the first granules.

14. The granular preparation according to claim 12, wherein the disintegrant is crospovidone and/or sodium carboxymethyl starch.

15. The granular preparation according to claim 14, wherein the disintegrant is crospovidone.

16. The granular preparation according to claim 1, further comprising a binder.

17. The granular preparation according to claim 16, wherein the binder is contained in the first granules.

18. The granular preparation according to claim 16, wherein the binder is hydroxypropylcellulose.

19. The granular preparation according to claim 1, wherein the granular preparation is granules for an oral suspension or a dry syrup.

20. The granular preparation according to claim 19, wherein the granular preparation is granules for an oral suspension.

21. The granular preparation according to claim 19, wherein the granular preparation is a dry syrup.

22. The granular preparation according to claim 1, wherein the granular preparation is used as an aqueous solution or an aqueous suspension.

23. An aqueous solution or an aqueous suspension of the granular preparation according to claim 1.

24. A method for producing a granular preparation, comprising
   i. a step of obtaining first granules by wet-granulating
      (A) edoxaban or a pharmacologically acceptable salt thereof,
      (B) D-mannitol,
      (C) pregelatinized starch,
      (D) crospovidone, and
      (E) hydroxypropylcellulose
      using water or an aqueous solution of the hydroxypropylcellulose (E),
   ii. a step of obtaining second granules by wet-granulating
      (F) 0.5 to 10% by weight of carmellose sodium with respect to the total weight of the preparation, and
      (G) 70 to 90% by weight of xylitol or sorbitol with respect to the total weight of the preparation
      using water or an aqueous solution of the carmellose sodium (F), and
   iii. a step of mixing the first granules and the second granules obtained.

25. The method according to claim 24, wherein the wet granulation is fluidized-bed granulation.

26. The method according to claim 24, wherein the ratio ($R_2/R_1$) of the median size of the second granules ($R_2$) to the median size of the first granules ($R_1$) is 0.75 to 1.75.

27. The method according to claim 24, wherein the median size (X50) of the first granules is 130 μm to 240 μm, and the median size (X50) of the second granules is 170 μm to 240 μm.

28. The method according to claim 24, wherein the granular preparation is granules for an oral suspension or a dry syrup.

29. The method according to claim 28, wherein the granular preparation is granules for an oral suspension.

30. The method according to claim 28, wherein the granular preparation is a dry syrup.

\* \* \* \* \*